United States Patent
Lappe et al.

(10) Patent No.: US 8,869,589 B2
(45) Date of Patent: Oct. 28, 2014

(54) DEVICE AND METHOD FOR DETERMINING THE FRICTION BETWEEN PLASTIC HOLLOW BODIES OF THE SAME MATERIAL COMPOSITION

(75) Inventors: Ulrich Lappe, Regensburg (DE); Florian Wickenhoefer, Bad Koetzting (DE); Stefan Hross, Barbing (DE); Jochen Forsthoevel, Regensburg (DE)

(73) Assignee: Krones AG, Neutraubling (DE)

( * ) Notice: Subject to any disclaimer, the term of this patent is extended or adjusted under 35 U.S.C. 154(b) by 348 days.

(21) Appl. No.: 13/353,623

(22) Filed: Jan. 19, 2012

(65) Prior Publication Data

US 2012/0186325 A1    Jul. 26, 2012

(30) Foreign Application Priority Data

Jan. 21, 2011   (DE) .......................... 10 2011 000 276

(51) Int. Cl.
*G01N 19/02* (2006.01)

(52) U.S. Cl.
CPC ...................... *G01N 19/02* (2013.01)
USPC .............................................................. 73/9

(58) Field of Classification Search
CPC ........... G01N 2033/0081; G01N 19/02; B29C 49/80; B29C 49/0005
USPC ............................................................... 73/9
See application file for complete search history.

(56) References Cited

U.S. PATENT DOCUMENTS

| | | | | |
|---|---|---|---|---|
| 1,887,527 A | * | 11/1932 | Spindel ................................ 73/7 |
| 3,033,019 A | * | 5/1962 | Oliver .................................. 73/9 |
| 3,323,889 A | * | 6/1967 | Carl et al. ....................... 65/60.2 |
| 3,382,702 A | * | 5/1968 | Ford .................................... 73/9 |
| 3,823,599 A | | 7/1974 | Litz et al. |
| 3,977,231 A | * | 8/1976 | Haehner et al. ...................... 73/9 |
| 3,985,026 A | * | 10/1976 | Griffin et al. ............... 73/150 R |
| 4,133,200 A | * | 1/1979 | Cray ................................. 73/10 |
| 4,187,714 A | * | 2/1980 | Cox et al. ............................ 73/9 |
| 4,194,387 A | * | 3/1980 | Hofbauer et al. ................... 73/9 |
| 4,507,953 A | * | 4/1985 | Vandermeerssche ............... 73/7 |
| 4,524,602 A | * | 6/1985 | Moore ................................. 73/9 |
| 5,245,856 A | * | 9/1993 | Pazzaglia et al. ................... 73/9 |
| 5,373,723 A | * | 12/1994 | Chou .................................. 73/9 |
| 5,377,526 A | * | 1/1995 | Diekmann et al. .................. 73/9 |
| 5,388,442 A | * | 2/1995 | Kumar et al. ..................... 73/10 |
| 5,736,630 A | * | 4/1998 | Welner ............................... 73/9 |

(Continued)

FOREIGN PATENT DOCUMENTS

| | | |
|---|---|---|
| CN | 2187791 Y | 1/1995 |
| CN | 2231418 Y | 7/1996 |

(Continued)

*Primary Examiner* — David A Rogers
(74) *Attorney, Agent, or Firm* — Simpson & Simpson, PLLC

(57) ABSTRACT

A device (1) and a method for determining the friction between plastic hollow bodies (2) with the same material composition. For this purpose, at least one plastic hollow body (2S) is rigidly clamped in parallel to its longitudinal axis (LS) by means of bilateral clamping jaws (4). A linearly moveable plastic hollow body (2B) lies on the plastic hollow body (2S). The linearly and not in parallel to the longitudinal axis moveable plastic hollow body (2B) is impinged with a force ($F_G$). The moveable plastic hollow body (2B) presses with the force ($F_G$) onto the rigidly clamped plastic hollow body (2S). The neck area (3) of the moveable plastic hollow body (2B) is connected with a force measurement unit (6).

23 Claims, 10 Drawing Sheets

(56) References Cited

U.S. PATENT DOCUMENTS

| | | | |
|---|---|---|---|
| 5,824,742 A * | 10/1998 | Shinohara | 525/88 |
| 6,321,586 B1 * | 11/2001 | Wojtowicz et al. | 73/9 |
| 6,397,672 B1 * | 6/2002 | Ramkumar | 73/159 |
| 6,408,678 B1 * | 6/2002 | Chopra et al. | 73/9 |
| 6,494,076 B1 * | 12/2002 | Gent et al. | 73/9 |
| 6,691,551 B2 * | 2/2004 | Otaki et al. | 73/9 |
| 6,854,316 B2 * | 2/2005 | Hage et al. | 73/9 |
| 7,506,542 B2 * | 3/2009 | Brouwers et al. | 73/150 A |
| 7,788,965 B2 * | 9/2010 | Arnold et al. | 73/9 |
| 2002/0194895 A1 | 12/2002 | Germinario et al. | |
| 2003/0113490 A1 * | 6/2003 | Jen | 428/35.7 |
| 2003/0152726 A1 * | 8/2003 | Stafford et al. | 428/35.7 |
| 2004/0097383 A1 * | 5/2004 | Kupper et al. | 508/233 |
| 2004/0122150 A1 * | 6/2004 | Quillen et al. | 524/424 |
| 2004/0228994 A1 * | 11/2004 | Stafford et al. | 428/36.4 |
| 2007/0119686 A1 * | 5/2007 | Divisi | 198/502.1 |
| 2009/0081397 A1 * | 3/2009 | Carvell et al. | 428/35.7 |

FOREIGN PATENT DOCUMENTS

| | | |
|---|---|---|
| DE | 234933 | 4/1986 |
| DE | 10023289 | 11/2001 |
| DE | 69836359 | 10/2007 |
| FR | 2727519 | 5/1996 |
| GB | 2187560 | 9/1987 |
| WO | 02/097401 A2 | 12/2002 |
| WO | 2007094704 | 8/2007 |

* cited by examiner

DEVICE AND METHOD FOR DETERMINING THE FRICTION BETWEEN PLASTIC HOLLOW BODIES OF THE SAME MATERIAL COMPOSITION

CROSS-REFERENCE TO RELATED APPLICATIONS

This patent application claims priority from German Patent Application DE 10 2011 000 276.6, filed on Jan. 21, 2011, which application is incorporated herein by reference.

FIELD OF THE INVENTION

The present invention includes a device for determining the friction between plastic hollow bodies with the same material composition.

In addition, this invention concerns a method for determining the friction between plastic hollow bodies with the same material composition.

BACKGROUND OF THE INVENTION

From the prior art, devices are known, which can be used to determine the friction value between a body and a substrate made of a different material. Also, devices are known from the prior art, which allow determining the friction value (rolling friction) between plastic hollow bodies with the same material composition.

The international patent application WO 2007/094704 A1 discloses a system for automatic control of the friction values of preforms, which are used with a blowing machine for manufacturing plastic bottles. PET plastic bottles are manufactured from said preforms. The system according to the invention allows to control automatically the fraction values between the preforms and to add liquid appropriately based on the determined measured values so that the friction value between the preforms can be set to a specific value. For this purpose, a rotating carrier in a chamber is provided. A specific braking value is measured, which is forwarded to a control station, from where liquid is then appropriately transferred into the chamber.

The British patent application GB 2 187 560 A discloses a device for measuring the surface friction. This device allows determining the friction forces, which occur at the surface of a container. For this purpose, the container is rotated with respect to a thrust impinged with a force. The braking force is measured, which the thrust exerts on a transducer via a lever. This method allows determining the different friction values at a can's periphery depending on the different coloured layers of the can.

U.S. Patent Application 2002/0194895 A1 discloses an analysis system, which allows determining the fraction between two bottles. The device suggested here allows determining the friction coefficient for plastic bottles, which do not have a planar surface. This device allows determining the coefficient of friction of plastic bottles or preforms with each other. For this purpose, a stationary sample contacts a rotating sample. A force is applied onto the stationary sample towards the rotating sample. By means of a computer, the required torque is determined at the time point when both probes slide against each other. Also, the torque amount is determined, which is required to keep a constant speed. Based on the torque measurements, the computer calculates the friction coefficient between both material samples.

Patent specification DD 234 933 A1 concerns a method and an assembly for determining coefficients of adhesion and sliding friction. The test materials are vehicle tires and the track surface acting on the vehicle tires. The test materials are pressed by means of articulated devices onto a friction surface provided for the measurement and shifted by means of gravity with constant contact pressure by mechanically acting equipment's. By shifting the test materials on the friction surface, the vertical pressing force, which acts on the test materials, and the required tractive force required for shifting the test materials are measured for determining the friction values.

BRIEF SUMMARY OF THE INVENTION

The task of the invention is to provide a transportable device, which allows at any location to determine the static friction between two plastic hollow bodies with the same material composition. The term static friction is also referred to as tackiness in everyday usage.

The task mentioned above is solved by a device, for determining the friction between plastic hollow bodies of the same material composition. Bilateral clamping jaws are provided, for rigidly clamping at least one first plastic hollow body parallel to its longitudinal axis. One second plastic hollow body, which is not parallel to the longitudinal axis of the rigidly clamped plastic hollow body, lies on the at least one first rigidly clamped plastic hollow body. A force being applied to the second moveable plastic hollow body, which lies on the at least one first rigidly clamped plastic hollow body with the applied force. A force measurement unit is provided to which a neck area of the second moveable plastic hollow body is rigidly connected.

Also, it is the task of the invention to provide a method that allows determining static friction between two plastic hollow bodies with the same material composition. The method should also allow to be used at the client's location, for example with a stretch blowing machine or at incoming inspection of the preforms.

The task mentioned above is solved by a method for determining the friction between plastic hollow bodies of the same material composition, comprising the following steps:

clamping at least one first plastic hollow body;

placing one second moveable plastic hollow body in such a way on the at least one rigidly clamped plastic hollow body that their longitudinal axis are not parallel to each other;

connecting a neck area of the second moveable plastic hallow body with a force measurement unit;

applying a force to the moveable plastic hollow body;

determining a maximum of a tractive force by shifting the force measurement unit linearly, wherein the maximum of a tractive force corresponds to the force at which the moveable plastic hollow body starts to slide on at least one first rigidly clamped plastic hollow body; and determining the maximum of the tractive force at different forces, which are applied to the moveable plastic hollow body.

The background of the present invention is that from a specified degree of tackiness of ready blown plastic bottles or preforms on, congestion can arise at diverse constrictions or running-ins of a line for manufacturing plastic bottles by means of the stretch blowing methods. A particularly vulnerable place for the formation of a congestion is the feeding of preforms or the infeed into a labeling machine. This congestion can cause stoppage of lines. In the worst case, certain combinations of preforms and plastic bottles even cannot be processed by means of a line. To ensure processing, however, this can lead to expensive retrofittings and to dissatisfaction at the client's side.

The devices according to the invention for determining the friction between plastic hollow bodies with the same material composition are designed in such a way that the friction values between plastic bottles and between preforms can be measured. Thereby, the preforms' diameter can range between 12 mm and 40 mm. The diameter of the plastic bottles manufactured from the preforms can range between 50 mm and 120 mm, so that the friction value between these plastic bottles can be still measured with the device according to the invention. There are no restrictions for the measurement with respect to the length of the preforms or the plastic bottles.

The device according to the invention is designed in such a way that at least one first plastic hollow body is clamped in parallel to its longitudinal axis by means of bilateral clamping jaws rigidly clamped in the device. On the at least one first rigidly clamped plastic hollow body lies a second plastic hollow body, which is not arranged in parallel to the vertical axis of the at least one first rigidly clamped plastic hollow body. The second plastic hollow body is therefore not moveable in parallel to the vertical axis of the rigidly clamped plastic hollow body. The second moveable plastic hollow body can be impinged with a predefined force, so that it lies with this force on the at least first rigidly clamped plastic hollow body. It is connected to a force measurement unit by means of a neck area of the second moveable plastic hollow body.

In the case that plastic hollow bodies are preforms, two preforms are rigidly clamped between both clamping jaws of the device. Another preform is then moveable arranged perpendicular to the longitudinal axis of the rigidly clamped preforms and lies on both rigidly clamped preforms.

In the case that the plastic hollow bodies are plastic bottles manufactured from preforms, it is sufficient that a plastic bottle is rigidly clamped between the bilateral clamping jaws of the device. Another plastic bottle lies movable, perpendicular to the rigidly clamped plastic bottle, on the longitudinal axis of the rigidly clamped plastic bottle. Both plastic bottles are impinged with an inner pressure for the measurement. The plastic bottles impinged with the inner pressure are closed with a corresponding shutter so that the inner pressure in the plastic bottles remains constant at least for the duration of the measurement.

The at least one first rigidly clamped plastic hollow body and the second plastic hollow body are moveable perpendicular to the longitudinal axis of the at least one first rigidly clamped plastic hollow body. The at least one first rigidly clamped plastic hollow body and the second plastic hollow body are impinged with a force $F_G$ (weight force) and thus pressed against each other. To apply the force, a pivoting lever arm is provided, which has at one free end at least one free rotating bearing. By means of a pivot axis, the pivoting lever arm is pivotably connected with the frame of the device. The at least one free rotating bearing then adjoins the second moveable plastic hollow body. For exerting a predefined force, which is used to press both plastic hollow bodies against each other in the device, the pivoting lever arm can be provided with weights to exert the required predefined force.

According to another embodiment, the pivoting lever arm is pivotably connected with the frame of the device via a pivoting axis. Also, the pivoting lever arm can be linearly adjustably connected by means of an oblong hole in the vertical direction with respect to a device base. The free rotating bearing then also adjoins the moveable plastic hollow body. By means of adjusting the pivoting lever arm in height, it is possible that the pivoting lever is adjusted to the diameter of the plastic hollow body to be examined. It is preferred that the lever arm is arranged parallel to the base of the device.

The device according to the invention has a slide that is designed such that it is connected with the device. The slide itself is designed such that it can be adjusted in the vertical direction. It is thereby possible that the force measurement unit can be shifted in linear direction of the slide to exert a tractive force onto the moveable plastic hollow body.

The force measurement unit and the neck area of the moveable plastic hollow body are coupled with a rigid connection.

To provide better transportation of the device according to the invention, it is designed in a modular fashion. The device then consists of a first and a second module, which are releasably connected to each other. The first module then carries the force measurement unit. The second module carries the plastic hollow body to be measured, the clamping jaws, with which at least one plastic hollow body can be rigidly clamped and the pivoting lever arm, which can be used to impinge the second moveable plastic hollow body with a predefined force.

The method according to the invention allows determining the friction (static friction) between plastic hollow bodies with the same material composition. For this purpose, at least one first plastic hollow body is first rigidly clamped. Another, second plastic hollow body, which in the end is moveable with respect to the first rigidly clamped plastic hollow body, is put on the first rigidly clamped plastic hollow body, so that their longitudinal axis are not parallel to each other. The neck area of the first moveable plastic hollow body is connected with a force measurement unit. The second moveable plastic hollow body is impinged with a force, so that the second moveable plastic hollow body is pressed against the first rigidly clamped plastic hollow body. The force measurement unit is finally shifted linearly and a maximum of the tractive force is determined. The maximum of the tractive force corresponds to the force at which the second moveable plastic hollow body starts to slide on the at least one first rigidly clamped plastic hollow body and thus overcomes the static friction between the plastic hollow bodies. The maximum of the tractive force to be used is determined at different forces with which the plastic hollow bodies are pressed against each other, and are composed of two subforces. The first subforce is required for overcoming the static friction and the second subforce serves to maintain sliding of the second moveable plastic hollow body.

The determined individual maxima of the tractive force are applied as a function of the force applied to the second moveable plastic hollow body. Subsequently, the points are connected with a straight line and the resulting intersection with the ordinate shows the static friction.

In the case that plastic bottles are to be measured with the method according to the invention, they are impinged with an inner pressure and closed at the neck area with a valve shutter.

For determining the static friction between the at least one first rigidly clamped plastic hollow body and the second moveable plastic hollow body, they are arranged with respect to each other in such a way that the surfaces get contact in a cylindrical section of the plastic hollow bodies.

It is of particular advantage, if the device according to the invention has a handy size and can be disassembled, so that it can be transported to the place of use in a conventional suitcase. For all required adjustments of the device with respect to clamping of at least one plastic hollow body, snap locks should be used, if possible, so that additional tools do not need to be employed. The force measurement unit connected with the moveable plastic hollow body is designed as tractive dynamometer. The force measurement unit is also attached to a slide adjustable in height so that it can also be adapted to the diameter of the plastic hollow body to be examined. By means of the slide, the force measurement unit is freely moveable in the horizontal direction with regard to the remaining measurement apparatus. For determining the retention force between the plastic hollow bodies to be measured, the slide needs to be moved in a fixed pull-off direction until the plastic hollow bodies detach from each other. The measured retention force can be read on the display of the dynamometer.

BRIEF DESCRIPTION OF THE DRAWINGS

Examples of embodiments of the invention, and the advantages thereof, will be explained in more detail below with reference to the appended figures. The size ratio of the individual elements with respect to each other in the figures does not always match the real size ratios since some forms are shown simplified and other parts are shown larger in relation to other elements for the purpose of better illustration.

FIG. 1 schematically shows the arrangement of the plastic hollow bodies to be measured if they are designed as preforms, wherein the acting balance of forces is also drawn in;

FIG. 2 schematically shows the arrangement of plastic hollow bodies in relation to each other, for the case that they are designed as plastic bottles, wherein the acting balance of forces for the measurement is also drawn in;

DETAILED DESCRIPTION OF THE INVENTION

Identical references are used for elements of the invention which are identical or which have the same function. Furthermore, for the sake of clarity, the individual figures contain only the references necessary for describing the respective figure. The represented embodiments are only examples of how the device according to the invention and the method according to the invention can be designed and are no final limitation of the invention.

Figure 1:
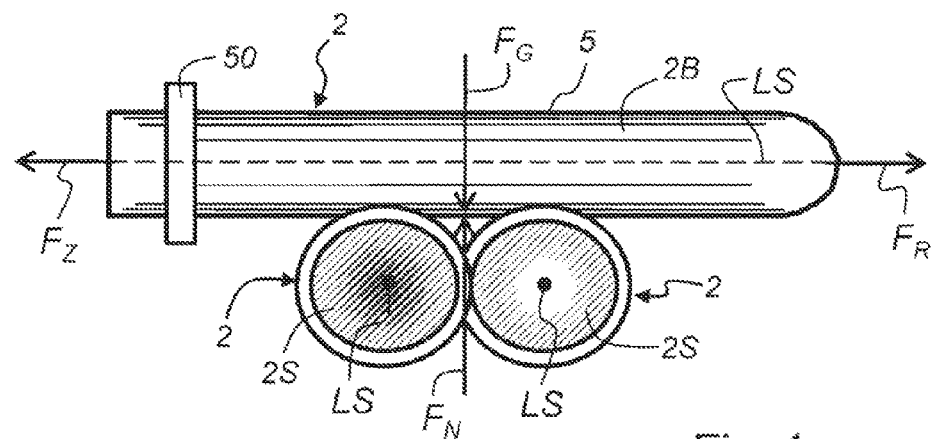

FIG. 1 schematically shows the arrangement of the plastic hollow bodies 2 in relation to each other in order to determine the static friction of the individual plastic hollow bodies 2. In the embodiment shown in FIG. 1, the plastic hollow bodies 2 are designed as preforms. The plastic hollow bodies 2 are then arranged in such a way that a second moveable plastic hollow body 2B lies on two first rigid plastic hollow bodies 2S. The longitudinal axis LS of the moveable plastic hollow body 2B is then arranged perpendicular to the longitudinal axis of the rigid plastic hollow bodies 2S. The moveable plastic hollow body 2B is thus essentially in contact with a substantially cylindrical circumferential surface 5 with the circumferential surface 5, which is also cylindrical, of the rigid plastic hollow bodies 2S. The moveable plastic hollow body 2B is impinged with a force $F_G$. A normal force $F_N$ counteracts this force $F_G$. A tractive force $F_Z$, which counteracts a static friction force $F_R$, acts on the moveable plastic hollow body 2B.

Figure 2:
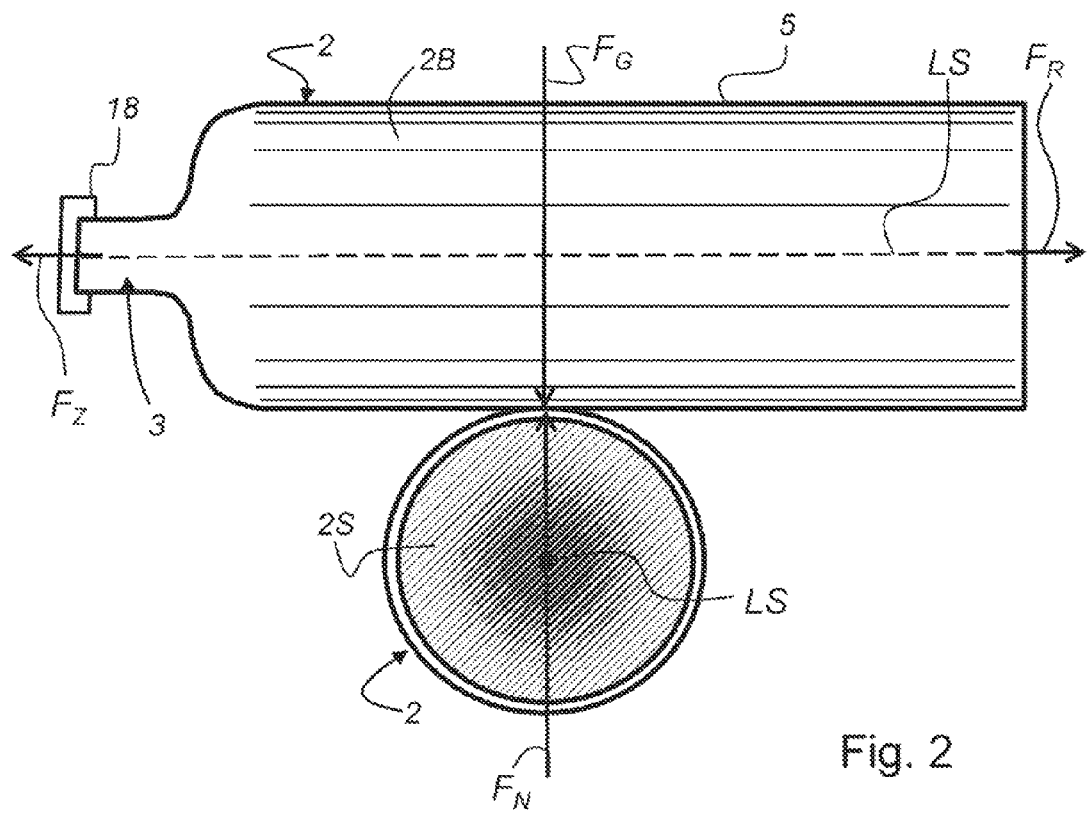

FIG. 2 describes the arrangement of the plastic hollow bodies 2 for the case that they are designed as plastic bottles. The plastic bottles are manufactured from preforms as described in FIG. 1. In the case of the arrangement of the plastic hollow bodies shown in FIG. 2 for the measurement, the same force distribution acts as already described in FIG. 1. For the case that the plastic hollow bodies 2 are plastic bottles, they are filled with a specified inner pressure P for the measurement. To make sure that the inner pressure P remains constant at least for the duration of measurement, the plastic hollow body 2 is closed at a neck area 3 with a valve shutter 18. The tractive force $F_Z$ acts therefore on the neck area 3 or on the valve shutter 18 of the moveable plastic hollow body 2B. The moveable plastic hollow body 2B and the rigid plastic hollow body 2S are arranged with respect to each other in such a way that their longitudinal axis LS are aligned perpendicular to each other and the circumferential surfaces 5 of the moveable plastic hollow body 2B and of the rigid plastic hollow body 2S touch each other.

Figure 3:
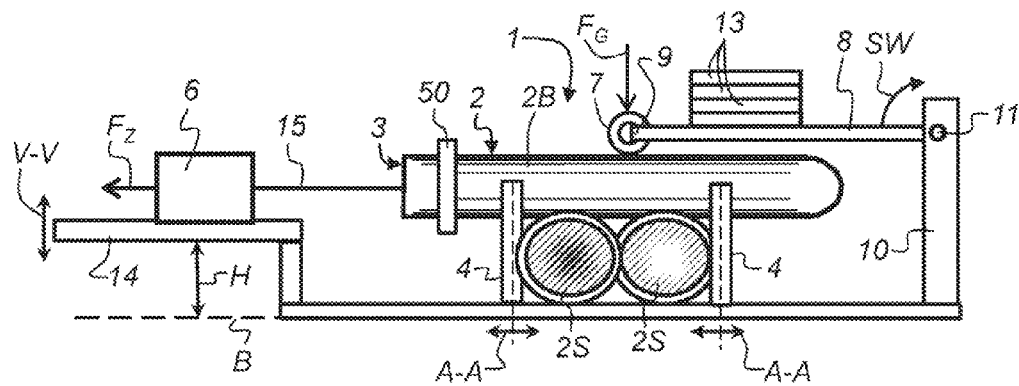
FIG. 3 schematically shows the device for measuring the static friction between plastic hollow bodies, wherein they are designed as preforms.

FIG. 3 shows a schematic structure of the device 1 according to the invention, with which the static friction between two rigidly clamped plastic hollow bodies 2S and a linearly moveable plastic hollow body 2B is measured. In the case that the plastic hollow bodies 2 are designed as preforms, it is recommended that two preforms are rigidly clamped. For the measurement, it is sufficient that a preform lies on the rigidly clamped preforms. The alignment of the plastic hollow bodies 2 with respect to each other is already described in FIG. 1. The force $F_G$, which is exerted on the moveable plastic hollow body 2B, is generated by means of a pivoting lever arm 8. The pivoting lever arm 8 is connected with the frame 10 of the device 1 through a pivoting arm 11. At least one bearing is attached at the free end 9 of the pivoting lever arm 8. Bearing 7 lies on the moveable plastic hollow body 2B. Bearing 7, for example, a bearing roll, is required to ensure free mobility of the moveable plastic hollow body 2B and thus not to exert additional undesired forces to the arrangement of the plastic hollow bodies 2 for the measurement. The force $F_G$ acting on the moveable plastic hollow body 2B can be varied by placing different weights 13 onto the lever arm 8. The rigid plastic hollow bodies 2S can be clamped in device 1 by means of at least two clamping jaws 4 that are moveable in the direction of the double arrow A-A. A force measurement unit 6 is mounted on a slide 14. The slide 14 can be adjusted along the vertical direction V-V in the height H in relation to a base B of the device 1. The displacement of the slide 13 in height H is required so that the tractive force, which is exerted on the moveable plastic hollow body 2b by means of the force measurement unit 6, acts essentially in parallel to the base B of the device 1 and centrally. The neck area 3 of the moveable plastic hollow body 2B is connected with the force measurement unit 6 with a rigid connection 15. In order that the rigid connection 15 can act on the moveable plastic hollow body 2B, the moveable plastic hollow body 2B can be provided with a closing cap (not represented here). For inserting new plastic hollow bodies 2 to be measured, the pivoting lever arm 8 can be pivoted with the pivoting axis 11 along the pivoting direction SW.

Figure 4:
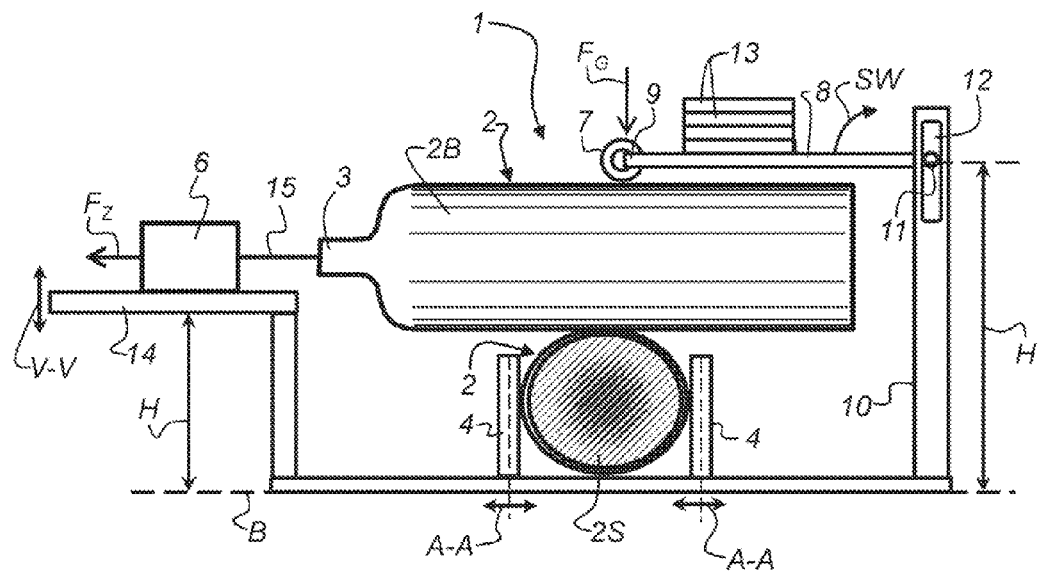
FIG. 4 schematically shows the device for measuring the static friction between plastic hollow bodies, wherein they are designed as plastic bottles.

FIG. 4 shows a schematic structure of the device 1 according to the invention, which is used to measure plastic hollow bodies 2 that are designed as plastic bottles, which are manufactured from preforms. The structure of device 1 for measuring the static friction between plastic bottles is analogous to the structure already described in FIG. 3. One difference is that in addition to the slide 14, which is adjustable in height H, the pivoting lever arm 8 can also be adjusted in height H with the oblong hole 12. The displacement of the pivoting arm 8 in relation to height H and base B of the device 1 is useful so that the lever arm 8 also acts on the moveable plastic hollow body 2B in parallel to the base B of device 1. With the adjustability of the pivoting lever arm 8 in relation to the height H, it is possible to adapt oneself to the different diameters of the plastic hollow bodies 2 to be measured.

Figure 5:
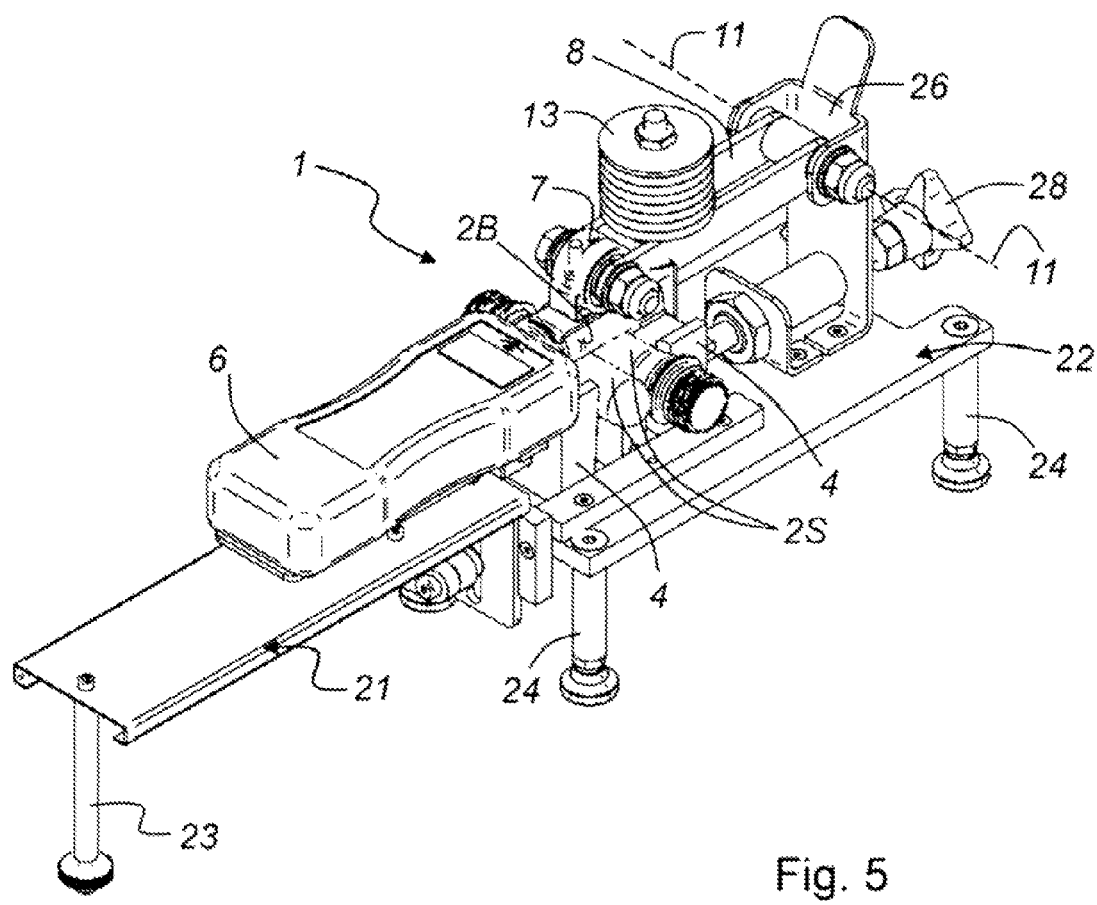
FIG. 5 shows a perspective view of the device according to the invention for measuring the static friction between plastic hollow bodies, wherein they are designed as preforms.

FIG. 5 shows a perspective view of an embodiment of the device 1 according to the invention, which is appropriate for measuring plastic hollow bodies 2, if these plastic hollow bodies 2 are preforms. The device according to the invention consists of a first module 21 and a second module 22, which are releasably connected with each other. The first module 21 carries the force measurement unit 6. The measuring unit 6 is designed as a tractive pressure dynamometer. The second module 22 carries the plastic hollow bodies 2 to be measured, which are rigidly clamped between the at least two moveable clamping jaws 3. The pivoting lever arm 8 with the bearing 7 lie on the moveable plastic hollow body 2B. Different weights can be placed on the pivoting lever arm 8. The pivoting axis 11 of the lever arm 8 is held in a preformed part 26. The preformed part 26 also carries an adjusting screw 28, which acts on the at least two moveable clamping jaws 4 to achieve thereby clamping of the rigid plastic hollow body 2S. The first module 21 is provided with at least one foot 23. Also, the second module 22 is provided with at least one foot 24. The feet 23 and 24 are designed to be adjustable in height, so that the first module 21 and the second module 22 can be adjusted with respect to their height and they are adaptable.

Figure 6:
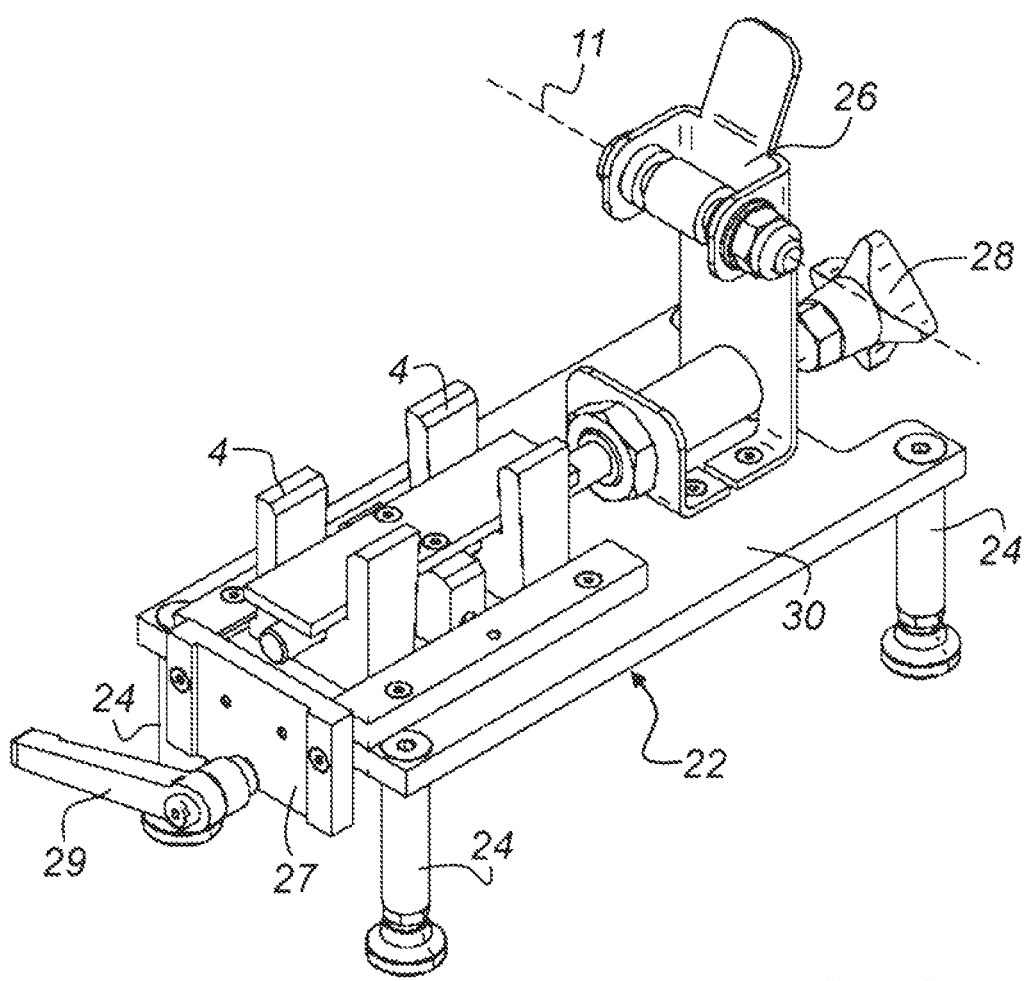
FIG. 6 shows a perspective view of the second module of the device, in which the preforms to be measured are inserted for the measurement.

FIG. 6 shows a perspective view of the second module 22 of the device 1 according to the invention for measuring the static friction between preforms, which represent the plastic hollow bodies 2 to be measured. As already described in FIG. 5, a preformed part 26 is attached to the mounting plate of the second module 22. The preformed part 26 carries the pivoting axis 11 for the lever arm (not represented here) and the adjusting screw 28 for moving the clamping jaws 4 so that sufficient clamping of the rigid plastic hollow bodies 2S in device 1 can be achieved. The mounting plate 30 also carries the feet 24 adjustable in height. A stop plate 27, in which a quick-release lever 29 sits, is attached on the side of the mounting plate 30 of the second module 22 facing away from the adjustable screw 28. The first module 21 can be releasably connected easily and in a time-efficient manner with the second module 22 using the quick-release lever 29.

Figure 7:
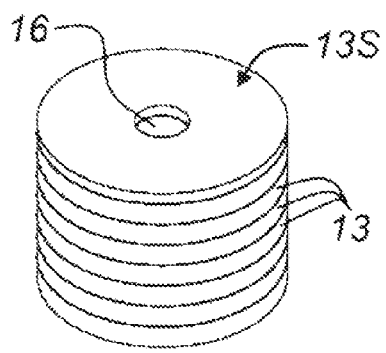
FIG. 7 shows a perspective view of a batch of weights, which can be put on the lever arm provided in the second module.

FIG. 7 shows a perspective view of a weight batch 13S, which can be placed on the pivoting lever arm (not represented here) to exert the required $F_Z$ to the moveable plastic hollow body 2B. The weight batch 13S consists of a plurality of disk-shaped individual weights 13, wherein each weight 13 has formed out a central borehole 16. By means of the individual weights 13, which can have different weights or the same weight, it is possible to adjust different forces $F_Z$, which act on the moveable plastic hollow body 2B through the pivoting lever arm 8.

Figure 8:
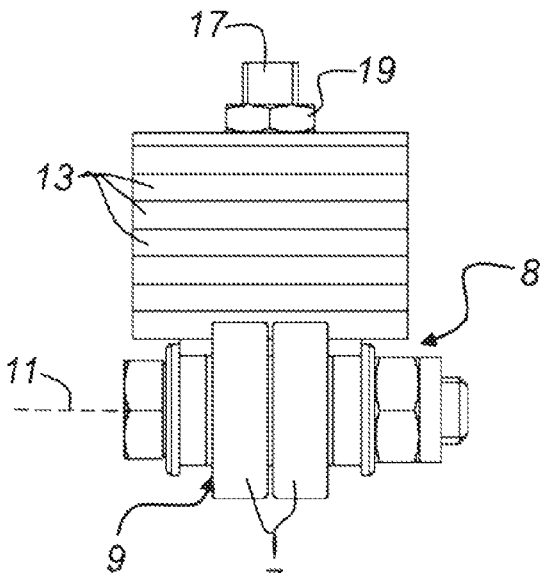
FIG. 8 shows a front view of the lever arm of the device according to the invention, where a batch of weights are put on the lever arm.

FIG. 8 shows a front view of an embodiment of the lever arm 8, which is used with the device 1 according to the invention. At the free end 9 of the lever arm 8 facing away from the pivoting axis 11, the lever arm 8 carries two freely rotatable bearings 7 in the embodiment represented here. As already mentioned, the freely rotatable bearings 7 lie on the circumferential surface 5 of the moveable plastic hollow body 2B. The individual weights 13 are placed on a mandrel 17. The weights 13 are fastened firmly to the lever arm 8 with a nut 19.

Figure 9:
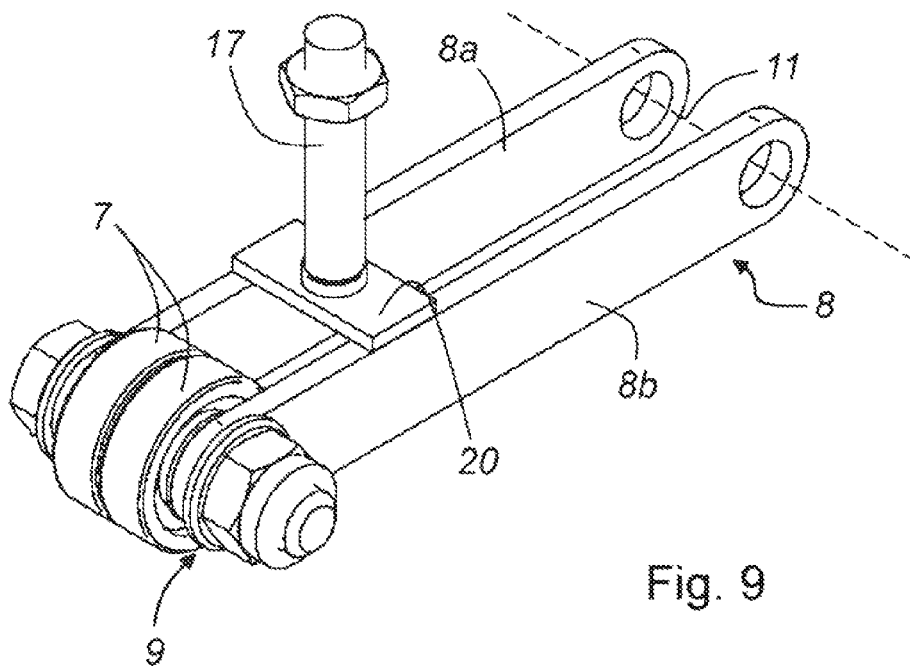
FIG. 9 shows a perspective view of the lever arm.

FIG. 9 shows a perspective view of the pivoting lever arm 8, which is used with the device 1 according to the invention. The pivoting lever arm 8 possesses a first arm 8a and a second arm 8B. The first arm 8a and the second arm 8b are connected with each other through a rigid bridge 20. The rigid bridge 20 carries the mandrel 17 for receiving the different weights 13. Both freely rotatable bearings 7 are also arranged between the first arm 8a and the second arm 8b of the pivoting level arm 8.

Figure 10:
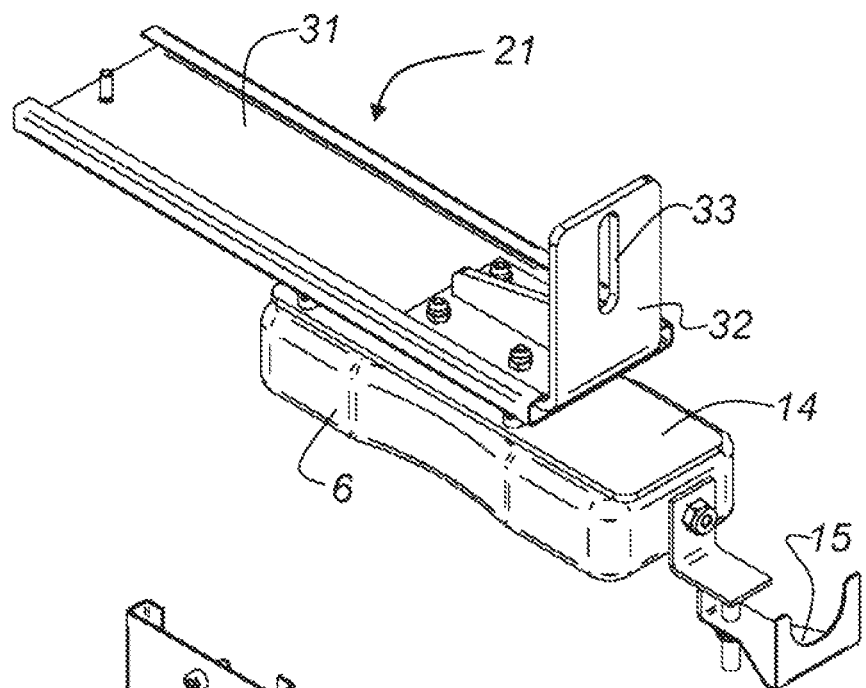
FIG. 10 shows a perspective view from below of the first module, which can be connected with the second module.
Figure 11:
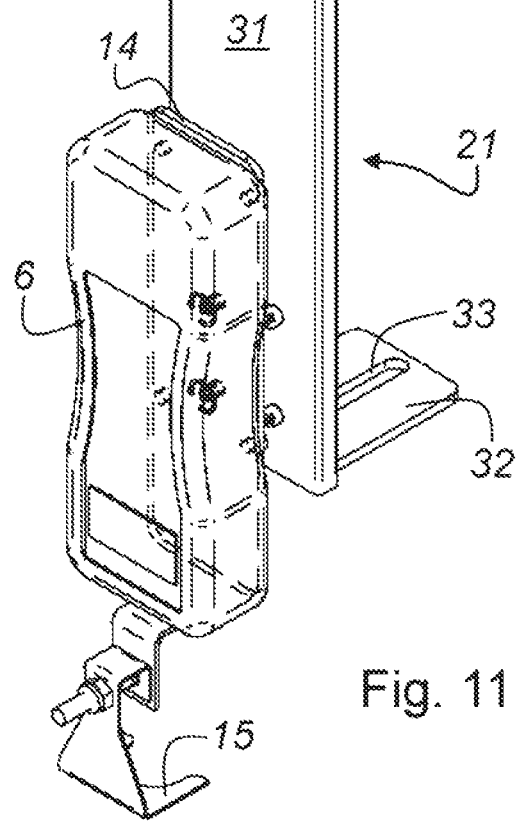
FIG. 11 shows a perspective top view onto the first module, which carries the force measurement unit.

FIGS. 10 and 11 show respectively a perspective view of the first module 21 from different angles. The first module 21 comprises a mounting plate 31, on which the slide 14 for the force measurement unit 6 sits. The force measurement unit 6 is moveable in the linear direction on slide 14. For attaching the first module 21 to the second module 22, a plate 32 is mounted onto the mounting plate 31 of the first module 21. An oblong hole 33 is formed in plate 32. The quick-release lever 29, with which the first module 21 and the second module can be connected in a detachable manner, grasps through this oblong hole. By means of oblong hole 33 it is possible to adjust the first module 21 in height with regard to the second module 22. The force measurement unit is connected with a rigid connection 15. The rigid connection 15 has the purpose to establish the connection from the force measurement unit 6 to the moveable plastic hollow body 2B. In the embodiment described in FIG. 10 and FIG. 11, the rigid connection 15 is designed in such a way that it grasps, for example, behind a supporting ring 50 (not represented here) of a preform.

Figure 12:
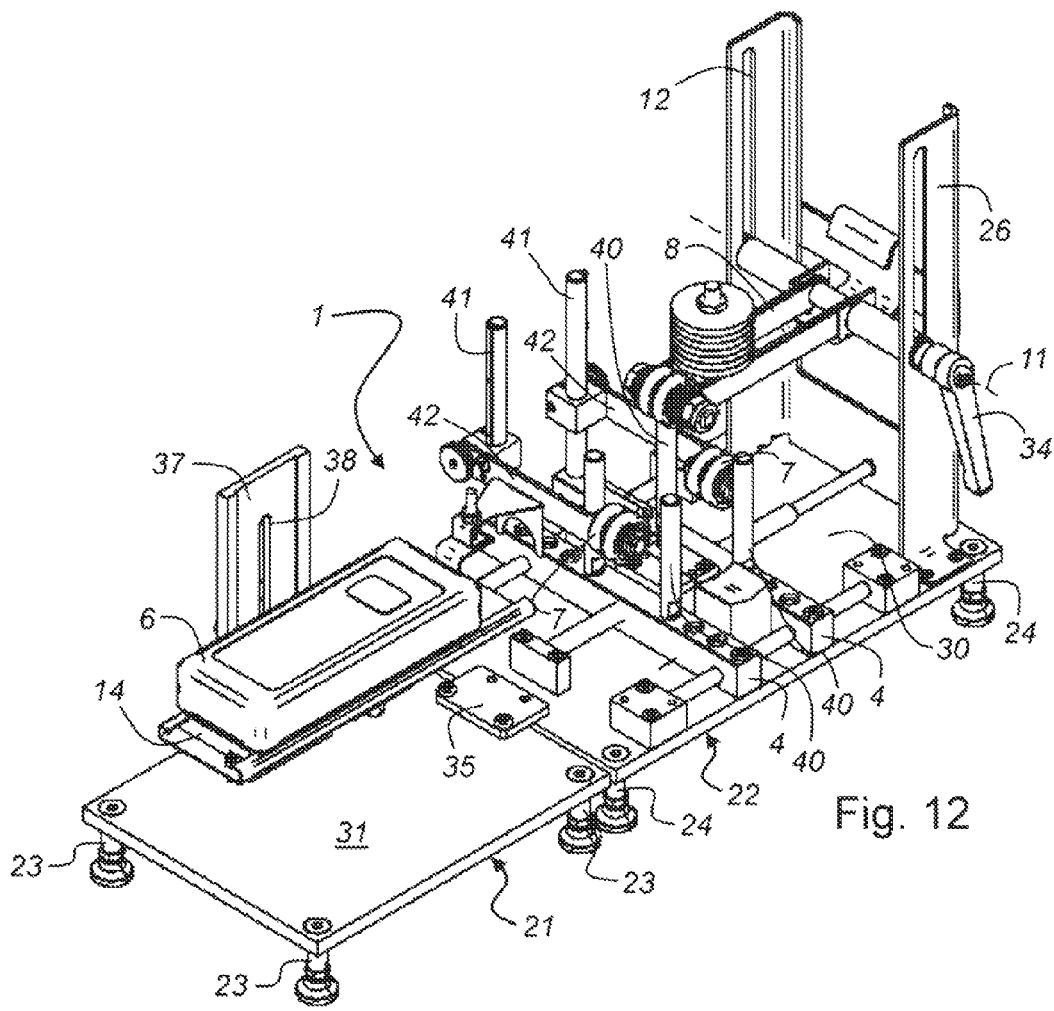
FIG. 12 shows a perspective view of the device according to the invention, which is designed for measuring the static friction between plastic hollow bodies, wherein the plastic hollow bodies consist of plastic bottles manufactured from preforms.

FIG. 12 shows a perspective view of a device for determining the static friction between plastic hollow bodies 2, wherein the device is suitable for plastic hollow bodies 2 that are designed as plastic bottles. The plastic bottles are manufactured from preforms. The device 1 according to the invention also comprises a first module 21 and a second module 22. The first module 21 comprises a mounting plate 31, which is provided with several feet 23. A holding plate 37, which has an oblong hole 38 formed in, is attached to the mounting plate 31. The slide 14 for the force measurement unit 6 can be attached to the holding plate 37. The slide 14 can be adjusted in height together with the force measurement unit 6 through the oblong hole 38. Using a strap 35, the first module 21 can be connected with the second module 22 of the device 1. The second module 22 is designed for measuring the static friction between plastic hollow bodies 2, which are available in the form of plastic bottles. A preformed part, in which the oblong hole 12 is provided, also lies on the base plate 30 of the second module 22. The pivoting axis 11 of the lever arm 8 can be adjusted in height in oblong hole 12. By means of a quick-release lever 34, the height of the pivoting level arm 8 adjusted in this way can be fastened. In the moveable clamping jaws 4, pins, which in the end clamp the rigid plastic hollow body 2S, can be inserted at different positions. A rod 41 is inserted respectively at one end of the clamping jaws 4. A supporting arm 42 adjustable in height is attached to each rod 41. Each of the supporting arms 42 adjustable in height also carries a bearing 7. The supporting arms 42 adjustable in height can be adjusted in such a way that the moveable plastic hollow body 2B lies on the bearings 7 of the supporting arms 42 and that they are at the same time in contact with the circumferential surface 5 of the rigid plastic hollow body 2S.

Figure 13:
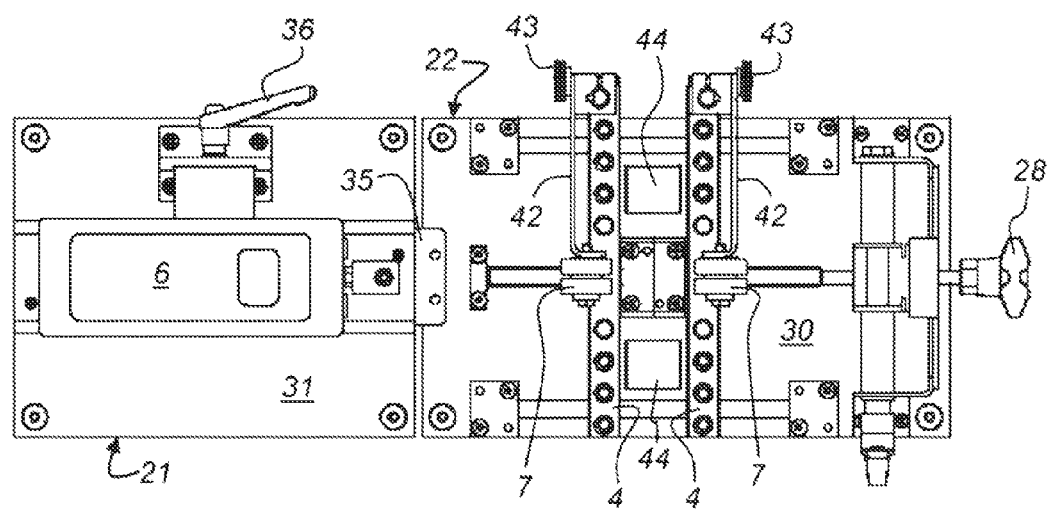
FIG. 13 shows a top view of the device represented in FIG. 12.

FIG. 13 shows a top view of the device 1 according to the invention, which is designed for determining the static friction between plastic hollow bodies 2, which have the shape of plastic bottles. The force measurement unit 6 lies on a slide 14 as already mentioned in the description of FIG. 12. The slide 14 can be displaced along a holding plate in height H. For the fixation of the correctly adjusted height, a quick-release lever 36 is provided. The second module 22 carries the adjustable clamping jaws 4 of the mounting plate 30. By means of the adjustable screw 28, the clamping jaws 4 can be moved towards or away from each other. The pins 40 sitting in the clamping jaws 4 hold in this way the plastic hollow body 2 or the plastic bottle to be examined. The plastic bottle moveable towards the force measurement unit 6 lies on the bearings 7, which are attached to corresponding holding arms 42. The holding arms 42 can be adjusted in height by means of the rods 41. By means of adjustable screws 43, the holding arms 42 can be fastened in the specified height H for the plastic bottles to be currently examined.

Figure 14:
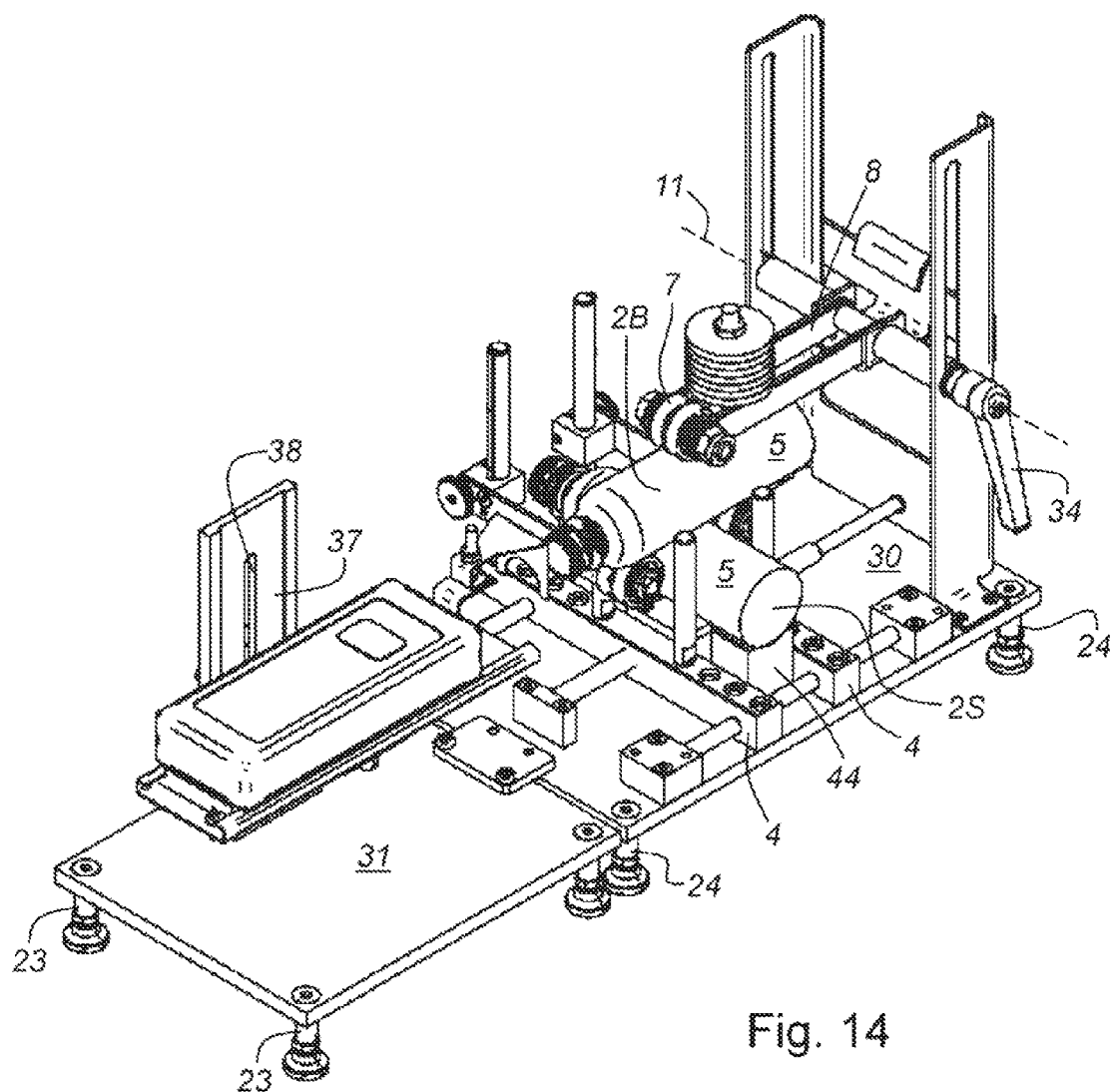
FIG. 14 shows the perspective view of the device shown in FIG. 13, in which the plastic bottles to be measured are also inserted in the second module of the device.

FIG. 14 shows a perspective view of the device 1 according to the invention, in which plastic bottles are inserted in the second module 22 so that the static friction between both plastic bottles can be determined. The rigid plastic hollow body 2S is clamped between the clamping jaws with the rods 40 provided for this purpose. The supporting arms 42 for the linearly moveable plastic hollow body 2B are adjusted in height at the rods 41 in such a way that the linearly moveable plastic hollow body 2B lies on the bearings 7 and touches at the same time the circumferential surface of the rigid plastic hollow body 2S. By means of the quick-release lever 34, the pivoting axis 11 of the lever arm 8 is adjusted in height in such a way that the pivoting arm 8 lies in parallel to the mounting plate of the second module 22. The feet 23 of the first module 21 and the feet 24 of the second module 22 can then be adjusted in height in such a way that the mounting plate 31 of the first module 21 is aligned with the mounting plate 30 of the second module 22 or they adjust to the same level.

Figure 15:
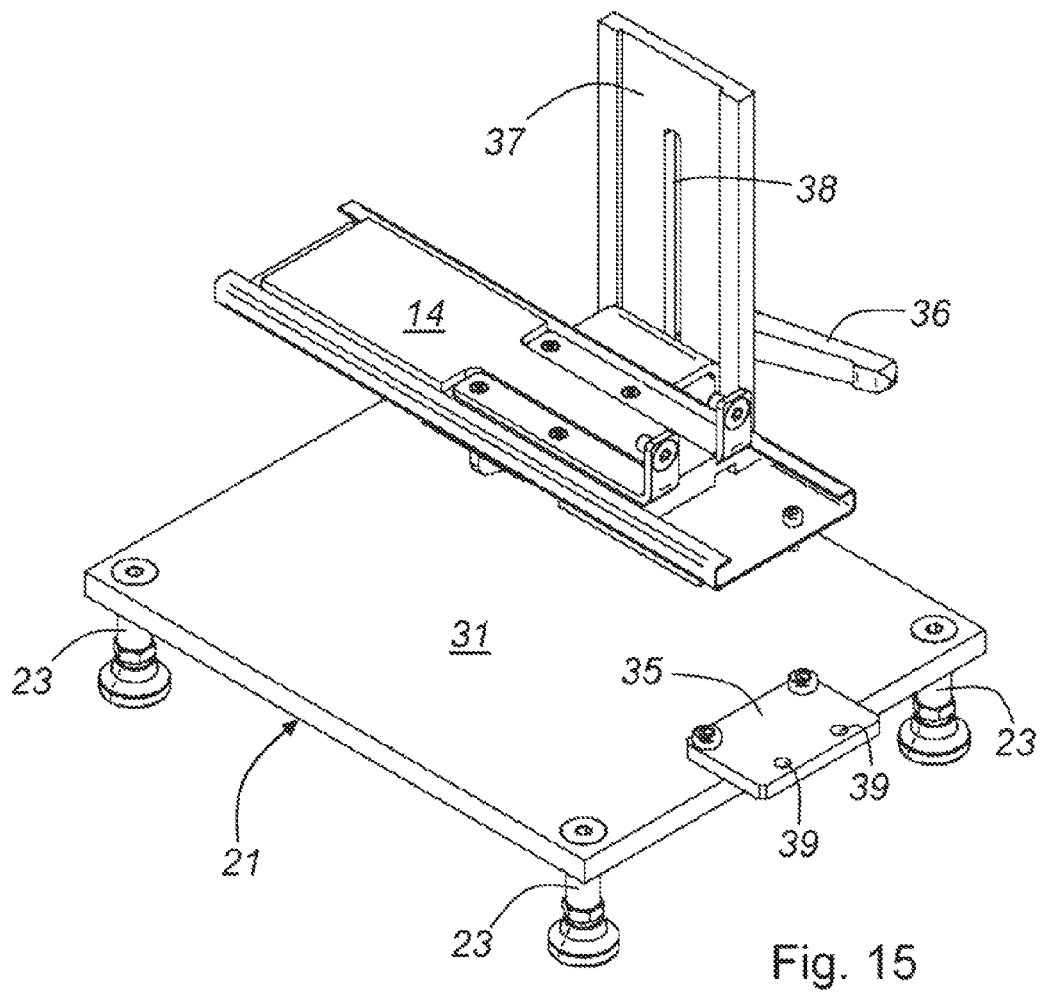
FIG. 15 shows a perspective view of the first module of the device according to the invention, in which the slide is designed to be adjustable in height for receiving the force measurement unit.

FIG. 15 shows a perspective view of the first module 21 of the device 1 according to the invention for measuring the static friction between plastic bottles. The mounting plate 31 of the first module 21 sits on several feet 23. The slide 14, which is attached to the mounting plate 31, is attached to the holding plate 31 in such a way that it can be adjusted in height. The displacement of slide 14 is effected through an oblong hole 38 formed out in holding plate 37. The fixation in the specified or desired height of the slide 14 is effected with a quick-release lever 36. A strap 35, in which at least two boreholes 39 are provided, is attached along the mounting plate 31. The boreholes act together with corresponding pins (not represented) in the mounting plate 31 of the second module 22. Therefore, it is possible to achieve in a quick and simple way a connection between the first module 21 and the second module 22.

Figure 16:
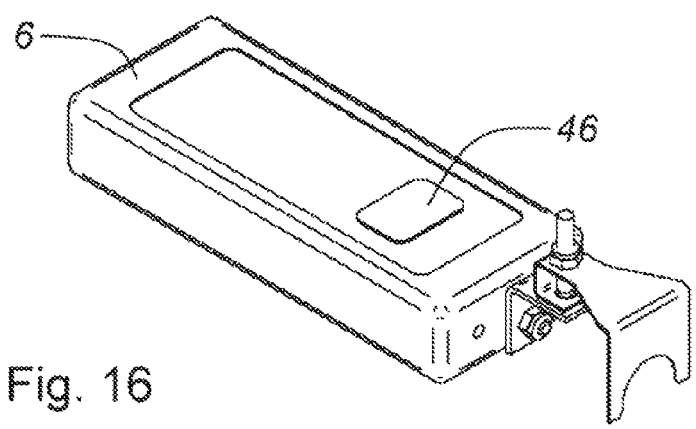
FIG. 16 shows a perspective view of the force measurement unit, which can be placed on the slide; and, FIG. 17 shows based on a diagram the different tackiness of the preforms depending on their treatment during manufacturing.

FIG. 16 shows a perspective view of the force measurement unit 6. The force measurement unit 6 is provided with a display 46, through which the maximum force, which is required to overcome the static friction between the rigid plastic hollow body 2S and the moveable plastic hollow body 2B is delivered.

Figure 17:
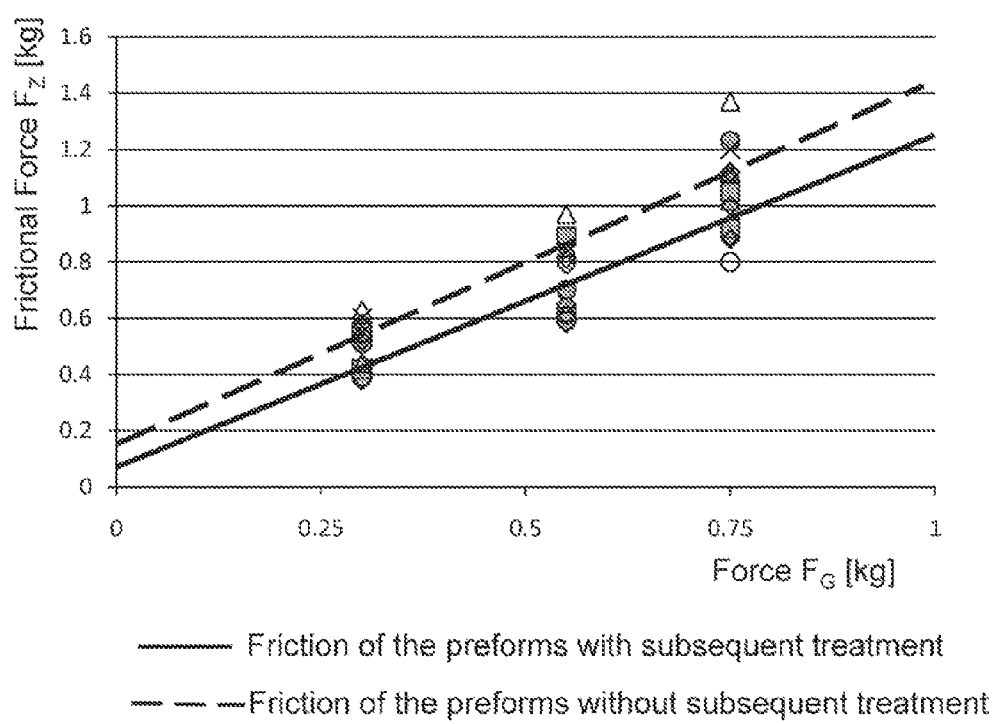

FIG. 17 shows a graphic representation of the dependency of the tackiness between preforms, which were submitted to different post-treatments after the injection moulding process. The force $F_G$, which acts on the moveable plastic hollow body 2B, is plotted in kilograms on the abscissa. As already described in the previous description, the force $F_G$ is directed to the moveable K plastic hollow body 2B by means of different weights on the pivoting arm 8. On the ordinate, the tractive force $F_Z$ is plotted, which is required to extract the moveable plastic hollow body 2B from the rigid plastic hollow body 2S. The solid line shows the values gained with preforms that received a post-treatment with the injection moulding process. The dashed curve shows the values for the preforms that received no post-treatment after the injection moulding process.

Following applies to the maximum tractive force $F_{Z,manx}$:

$$F_{Z,max} = \mu_H F_N + \mu_G F_N$$

$F_{Z,max}$ then stands for the maximum tractive force, which corresponds to the negative maximum holding force $F_{R,max}$. $\mu_H$ corresponds to the static friction value, which exists between two plastic hollow bodies 2 of the same batch and $\mu_G$ corresponds to the coefficient of sliding friction.

As FIG. 17 shows, there are clear differences. The preforms, which received a post-treatment, have a low tackiness with respect to each other. The force measurement unit 6 is used to measure a maximum tractive force $F_{Z,max}$, which is required to extract the moveable plastic hollow body 2B from the rigid plastic hollow body 2S. The maximum force $F_{Z,max}$ depends on the force $F_G$, which acts through the pivoting lever arm 8 onto the moveable plastic hollow body 2B. The static friction value can be determined by transferring the points determined to a coordinate system and connecting them with a straight line. The intersection of the straight line with the ordinate is then a value for the static friction or tackiness.

It is possible with the device 1 according to the invention to measure preforms or plastic bottles with any length. The device according to the invention also has a handy size and can be transported in a suitcase without the need to disassemble it. In the case of the device for measuring the static friction between the plastic bottles it is beneficial that the first module 21 and the second module 22 can be separated from each other. The devices according to the inventions should be preferably employed at construction sites and at client premises, where there are problems with adhesive preforms or adhesive plastic bottles. Another field of use of the device according to the invention is the incoming goods inspection for preforms in order to check the framework conditions of the manufacturer's preforms and to determine their quality. Based on the checked quality of the preforms delivered, it is then possible to draw conclusions about the workability of the preforms in a stretch blowing machine or in a complete line.

The invention was described with reference to preferred embodiments. However, it is for imaginable for a person skilled in the art that modifications or changes of the invention can be performed without leaving the scope of protection of the following claims.

LIST OF REFERENCE NUMERALS

1 Device
2 Plastic hollow body
2B First moveable plastic hollow body

2S Second rigidly clamped plastic hollow body
3 Neck area
4 Clamping jaws
5 Cylindrical circumferential surface
6 Force measurement unit
7 Bearing
8 Pivoting lever arm
8a First arm
8b Second arm
9 Free end
10 Frame of the device
11 Pivoting axis
12 Oblong hole
13 Weights
13S Weight batch
14 Slide
15 Rigid connection
16 Central borehole
17 Mandrel
18 Valve shutter
19 Nut
20 Rigid bridge
21 First module
22 Second module
23 Foot first module
24 Foot second module
26 Preformed part
27 Stop plate
28 Adjustable screw
29 Quick-release lever
30 Mounting plate second module
31 Mounting plate first module
32 Plate
33 Oblong hole
34 Quick-release lever
35 Strap
36 Quick-release lever
37 Holding plate
38 Oblong hole
39 Boreholes
40 Pins
41 Rod
42 Supporting arm
43 Adjustable screw
44 Support block
46 Display
50 Supporting ring
B Base of the device
$F_G$ Force onto the plastic hollow body
$F_N$ Normal force
$F_R$ Static friction force
$F_Z$ Tractive force
H Height
LS Longitudinal axis
SW Pivoting direction
A-A Direction of the movement of the clamping jaws
V-V Vertical direction

What is claimed is:

1. A device for determining the friction between plastic hollow bodies of the same material composition, comprising:
bilateral clamping jaws, for rigidly clamping at least one first plastic hollow body parallel to its longitudinal axis;
one second plastic hollow body, which is not parallel to the longitudinal axis of the rigidly clamped plastic hollow body, lies on the at least one first rigidly clamped plastic hollow body;
a force being applied to the second moveable plastic hollow body, which lies on the at least one first rigidly clamped plastic hollow body with the applied force;
a force measurement unit to which a neck area of the second moveable plastic hollow body is connected; and,
a slide being connectable with the device, wherein the slide can be adjusted in a vertical direction and wherein the force measurement unit at the slide can be linearly shifted towards a tractive force.

2. The device recited in claim 1, wherein a pivoting lever arm is provided and several weights are placeable on the pivoting lever arm, which has at one free end and at least one free rotating bearing is pivotably connected by means of a pivoting axis with a frame of the device and wherein the at least one free rotating bearing adjoins the second moveable plastic hollow body.

3. The device recited in claim 1, wherein a pivoting lever arm is provided and several weights are placeable on the pivoting lever arm, which has at one free end and at least one free rotating bearing is pivotably connected by means of a pivoting axis with a frame of the device and is connected in a linearly adjustable manner through an oblong hole in a height with respect to a base of the device and wherein at least one free rotating bearing adjoins the second moveable plastic hollow body.

4. The device recited in claim 1, wherein the at least one first plastic hollow body and the second moveable plastic hollow body are plastic bottles manufactured from preforms and one plastic bottle among the at least one first plastic hollow body is rigidly clamped between the bilateral clamping jaws and wherein the second moveable plastic bottle is moveable perpendicular to the longitudinal axis of the rigidly clamped plastic bottle and lies on the rigidly clamped plastic bottle.

5. The device recited in claim 4, wherein the plastic bottle is impinged with an internal pressure.

6. The device recited in claim 1, wherein the device has a first module and a second module, which are detachably connected with each other.

7. The device recited in claim 6, wherein the first module carries the force measurement unit.

8. The device recited in claim 6, wherein the second module carries the at least one first plastic hollow body to be measured, the clamping jaws for the rigidly clamped at least one first plastic hollow body and the pivoting lever arm for applying a force to the second moveable plastic hollow body.

9. The device according to claim 6, wherein the device has a first module and a second module, which are detachably connected with each other.

10. The device according to claim 9, wherein the first module carries the force measurement unit.

11. The device according to claim 9, wherein the second module carries the second preform to be measured, the clamping jaws for the rigidly clamped at least one first preform and the pivoting lever arm for applying a force to the moveable second preform.

12. A method for determining the friction between plastic hollow bodies of the same material composition, comprising the following steps:
clamping at least one first plastic hollow body;
placing one second moveable plastic hollow body in such a way on the at least one rigidly clamped plastic hollow body that their longitudinal axis are not parallel to each other;
connecting a neck area of the second moveable plastic hallow body with a force measurement unit;
applying a force to the moveable plastic hollow body;

determining a maximum of a tractive force by shifting the force measurement unit linearly, wherein the maximum of a tractive force corresponds to the force at which the moveable plastic hollow body starts to slide on at least one first rigidly clamped plastic hollow body; and
determining the maximum of the tractive force at different forces, which are applied to the moveable plastic hollow body.

13. The method recited in claim 12, wherein the maxima of the tractive force are applied as a function of the force, which is applied to the moveable plastic hollow body, the points are connected in the coordinate system by a straight line and the resulting intersection of the straight line can be read with the ordinate as a measure for the static friction or tackiness.

14. The method recited in claim 12, wherein the different forces are applied by placing several weights on a pivoting lever arm and the lever arm adjoins with least one free rotating bearing of the pivoting lever arm the second moveable plastic hollow body.

15. The method recited in claim 12, wherein the plastic hollow bodies are preforms and two preforms are rigidly clamped and wherein a preform is moved perpendicular to the longitudinal axis of both rigidly clamped preforms for determining the maximum tractive force.

16. The method recited in claim 12, wherein the plastic hollow bodies are plastic bottles manufactured out of preforms and one plastic bottle is rigidly clamped and wherein a plastic bottle is moved perpendicular to the longitudinal axis of the rigidly clamped plastic bottle for determining the maximum tractive force.

17. The method recited in claim 16, wherein the plastic bottles are impinged with an inner pressure and closed at the neck area with a valve shutter.

18. The method recited in claim 16, wherein the at least one rigidly clamped plastic hollow bottle and the moveable plastic hollow bottle are arranged to each other in such a way that their surfaces touch each other in a cylindrical section of the bodies plastic hollow bottles.

19. A device for determining the friction between preforms of the same material composition, comprising:
   bilateral clamping jaws, for rigidly clamping two preforms parallel to its longitudinal axis;
   one third preform, which is not parallel to the longitudinal axis of the rigidly clamped two preforms, lies on the two rigidly clamped preforms;
   a force being applied to the third moveable preform, which lies on the two rigidly clamped preforms with an applied force; and
   the force measurement unit to which a neck area of the third moveable preform is connected.

20. A device for determining the friction between preforms of the same material composition, comprising:
   bilateral clamping jaws, for rigidly clamping at least one first preform parallel to its longitudinal axis;
   a second preform, which is not parallel to the longitudinal axis of the rigidly clamped preform, lies on the rigidly clamped preform;
   a force being applied to the second moveable preform, which lies on the at least one first clamped preform with the applied force; and,
   a force measurement unit to which a neck area of the second preform is connected.

21. The device according to claim 20, wherein a pivoting lever arm is provided and several weights are placeable on the pivoting lever arm, which has at one free end and at least one free rotating bearing is pivotably connected by means of a pivoting axis with a frame of the device and wherein the at least one free rotating bearing adjoins the second moveable preform.

22. The device according to claim 20, wherein a pivoting lever arm is provided and several weights are placeable on the pivoting lever arm, which has at one free end and at least one free rotating bearing is pivotably connected by means of a pivoting axis with a frame of the device and is connected in a linearly adjustable manner through an oblong hole in a height with respect to a base of the device and wherein at least one free rotating bearing adjoins the second moveable preform.

23. A device for determining the friction between plastic hollow bodies of the same material composition, comprising:
   bilateral clamping jaws, for rigidly clamping at least one first plastic hollow body parallel to its longitudinal axis;
   one second plastic hollow body, which is not parallel to the longitudinal axis of the rigidly clamped at least one first plastic hollow body, lies on the rigidly clamped at least one first plastic hollow body;
   a force being applied to the second moveable plastic hollow body, which lies on the rigidly clamped at least one first plastic hollow body with the applied force;
   a force measurement unit to which a neck area of the second moveable plastic hollow body is connected;
   a pivoting lever arm, wherein several weights are placeable on the pivoting lever arm; and
   at least one free rotating bearing defines a pivoting axis of the pivoting lever arm, wherein the at least one free end of the pivoting lever arm is pivotably connected by means of the rotating bearing with a frame of the device and the at least one free is movable in a linearly height adjustable manner through an oblong hole with respect to a base of the device, wherein at least one free rotating bearing of the pivoting lever adjoins the second moveable plastic hollow body.

* * * * *